United States Patent [19]
Hayafuji et al.

[11] Patent Number: 5,106,364
[45] Date of Patent: Apr. 21, 1992

[54] SURGICAL CUTTER

[75] Inventors: Mineki Hayafuji; Yoshihiko Hanamura; Satoru Niimura, all of Tokyo, Japan

[73] Assignee: Kabushiki Kaisha Topcon, Tokyo, Japan

[21] Appl. No.: 545,494

[22] Filed: Jun. 29, 1990

[30] Foreign Application Priority Data

Jul. 7, 1989 [JP] Japan .................. 1-174122
Jul. 7, 1989 [JP] Japan .................. 1-174124

[51] Int. Cl.⁵ .............................................. A61B 17/32
[52] U.S. Cl. ...................................... 604/22; 606/171; 30/208; 30/241
[58] Field of Search ............... 606/171, 170; 128/751, 128/752, 755; 604/22; 30/241, 208-210

[56] References Cited

U.S. PATENT DOCUMENTS 4,246,902  1/1981  Martinez ................ 606/171 X
4,846,192  7/1989  MacDonald .............. 606/171 X

FOREIGN PATENT DOCUMENTS 1116465  6/1968  United Kingdom ............... 128/752

*Primary Examiner*—Michael H. Thaler
*Attorney, Agent, or Firm*—Foley & Lardner

[57] ABSTRACT

A surgical cutting instrument having an outer tubular member with a closed distal end, and an aperture therein which is adjacent to the closed distal end and which is in communication with the hollow of the outer tubular member. The instrument also includes an inner tube slidably disposed in the outer tube such that it reciprocates between first and second positions. The instrument also has a suction device which draws a portion of an object inwardly through the aperture. The inner tubular member has first and second edges which cooperate with the aperture such that when the suction device draws a first portion of the object into the aperture, the first edge cuts this portion away as the inner tubular member moves from the first position to the second position. However, when the suction device draws a second portion of the object into the aperture, the second edge cuts this portion away as the inner tubular member moves from the first position to the second position.

5 Claims, 7 Drawing Sheets

SURGICAL CUTTER

BACKGROUND OF THE INVENTION

1. Field of the Invention

The present invention generally relates to an in vivo surgical instrument and, more particularly, to the surgical instrument suited, but not exclusively limited thereto, for use in ophthalmic surgical operations for the removal of the diseased vitreous or in the treatment of a cataract.

2. Description of the Prior Art

It is well known that in an opthalmic surgical operation for the removal of the diseased vitreous or for the treatment of cataract, a surgical cutting instrument is utilized to remove prolapsed anterior vitreous. According to the state of art, the surgical cutting instrument is available in various types. One exemplary surgical cutting instrument comprises an outer tube having a closed distal end, and an inner tube having a distal end and being axially slidably inserted in the outer tube. The outer tube has a perforation defined therein at a position axially inwardly of the distal end thereof. The inner tube in the outer tube is adapted to be reciprocatingly moved axially within the outer tube. The distal end of the inner tube and a peripheral lip region defining the aperture in the outer tube cooperate with each other to provide a scissor action when the inner tube is axially moved relative to the outer tube to cut an affected tissue. The removed affected tissue is then sucked outwardly through the inner tube under the influence of a sucking force developed in the tube system.

In this known surgical cutting instrument, the cutting of the affected tissue takes place in a direction counter to the direction in which the sucking force acts, that is, in a direction confronting the closed distal end of the outer tube. Accordingly, it is necessary that the aperture defined in the outer tube adjacent the closed distal end be closed by a distal end portion of the inner tube during the stroke of movement of the inner tube.

Considering that the distal end of the outer tube is closed, and that when the inner tube closes the aperture in the outer tube subsequent to the cutting of the affected tissue, the affected tissue removed tends to be pushed into a space delimited between the closed distal end of the outer tube and the distal end of the inner tube to such an extent as to result in an occlusion. Once this occlusion occurs in the tube system, no surgical operation can be carried out without retraumatization.

Also, the cutting of the affected tissue and the suction of the removed tissue are correlated with each other and, therefore, it is desirable that the direction in which the cutting takes place, and the direction in which the removed tissue is sucked for the discharge thereof to be removed from the tube system be identical with each other in order to improve cutting efficiency.

Once the aperture defined in the outer tube adjacent the closed distal end is closed by the inner tube in the manner as hereinabove described, the eventual withdrawal of the tube system of the surgical cutting instrument from the eyeball, or the positional adjustment of the tube system within the eyeball may often result in an undesirable pull of the retina, vascular tissue or the like, by being sandwiched between the outer and inner tubes which may result in retraumatization.

In addition, in order to assure a safe removal of the affected tissue in the eyeball, it is required that the inner and outer tubes fit substantially perfectly into one another being capable of being slid with respect to each other. However, the substantially perfect fit between the outer and inner tubes requires time-consuming and complicated machining processes and assemblage, and therefore, the problem associated with the undesirable pull of sound tissue which is peripheral to the affected tissue, cannot be avoided. Accordingly, a compromise is that one side edge of the peripheral lip region defining the aperture in the outer tube is so shaped as to achieve a scissor action in cooperation with a peripheral edge at the distal end of the inner tube as the latter is moved past the aperture.

Thus, the prior art surgical cutting instrument has an additional problem in that the cutting performance is relatively low enough to substantially reduce a safety factor.

Accordingly, the present invention has been devised to provide an improved and safe surgical cutting instrument which does not cause retraumatization and which is capable of exhibiting a relatively high cutting efficiency for a substantially prolonged period of use.

SUMMARY OF THE INVENTION

To this end, the present invention in one aspect provides a surgical cutting instrument which comprises an outer tubular member having a distal end closed and also having an aperture defined therein adjacent the distal end in which is communication with the hollow of the outer tubular member, and an inner tubular member having a longitudinal axis parallel to the longitudinal axis of the outer tubular member and also having an open distal end disposed within the outer tubular member for axial sliding movement between first and second positions and for cooperation with the outer tubular member to provide a scissor action thereby cut an object to be removed, which has protruded inwardly through the aperture in the outer tubular member, during a reciprocating motion of the inner tubular member relative to the outer tubular member. The aperture in the outer tubular member is delimited by distal and proximal edges opposite to each other in a direction parallel to the longitudinal axis thereof, whereas the inner tubular member has an edge defined therein adjacent the distal end thereof so as to extend perpendicular to the longitudinal axis thereof while facing frontwards. One of the distal and proximal edges delimiting the aperture in the outer tubular member, which is positioned on one side conforming to the direction in which the object is sucked, is utilized to cut the object in cooperation with the inner tubular member.

Preferably, one of the distal and proximal edges delimiting the aperture in the outer tubular member may have an edge face lying perpendicular to the longitudinal axis thereof.

Also preferably, the inner tubular member may have an aperture defined therein adjacent to the distal end and delimited by distal and proximal edges opposite to each other in a direction parallel to the longitudinal axis thereof so that at least a portion of the aperture in the inner tubular member may be in communication with the aperture in the other tubular member regardless of the position of the inner tubular member relative to the outer tubular member between the first and second positions.

According to another aspect of the present invention, the present invention provides a surgical cutting instrument which comprises an outer tubular member having a closed distal end and also having a first aperture defined therein adjacent the distal end in communication with the hollow of the outer tubular member and delimited by distal and proximal edges opposite to each other in a direction parallel to the longitudinal axis thereof, and an inner tubular member having a longitudinal axis parallel to the longitudinal axis of the outer tubular member and also having an open distal end and accommodated within the outer tubular member for axial sliding movement between first and second positions and cooperable with the outer tubular member to provide a scissor action thereby to cut an object to be removed, which has protruded inwardly through the aperture in the outer tubular member, during a reciprocating motion of the inner tubular member relative to the outer tubular member. The inner tubular member has first and second edges defined therein adjacent the distal end thereof in opposition to each other, each of said first and second edges having an edge face lying generally perpendicular to the longitudinal axis thereof. The first edge of the inner tubular member is utilized to cut a portion of the object during the axial movement of the inner tubular member from the first position, towards the second position whereas the second edge is utilized to cut another portion of the object during the axial movement of the inner tubular member from the second position towards the first position.

Preferably, each of the distal and proximal edges delimiting a the aperture in the outer tubular member may have an edge face inclined downwardly towards the longitudinal axis thereof so as to define a respective acute angled edge.

The inner tubular member may also have a second aperture defined therein adjacent the distal end thereof, said second aperture in the inner tubular member being delimited by distal and proximal edges opposite to each other in a direction parallel to the longitudinal axis of said inner tubular member. In this case, the first and second edges in the inner tubular member are constituted respectively by the distal and proximal edges delimiting the second aperture in the inner tubular member.

Also preferably, at least the distal edge of the first aperture in the outer tubular member may be rounded with a substantially intermediate portion thereof protruding towards the proximal edge of the first aperture in the outer tubular member. Alternatively, the distal and proximal ends of the first aperture in the outer tubular member may be rounded with respective substantially intermediate portions protruding towards each other in a direction parallel to the longitudinal axis of the outer tubular member.

BRIEF DESCRIPTION OF THE DRAWINGS

In any event, the present invention will become more clearly understood from the following description of the preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined solely by the appended claims. In the accompanying drawings, like reference numerals are used to denote like parts throughout the several views, and:

DETAILED DESCRIPTION OF THE PREFERRED EMBODIMENTS

Figure 1:
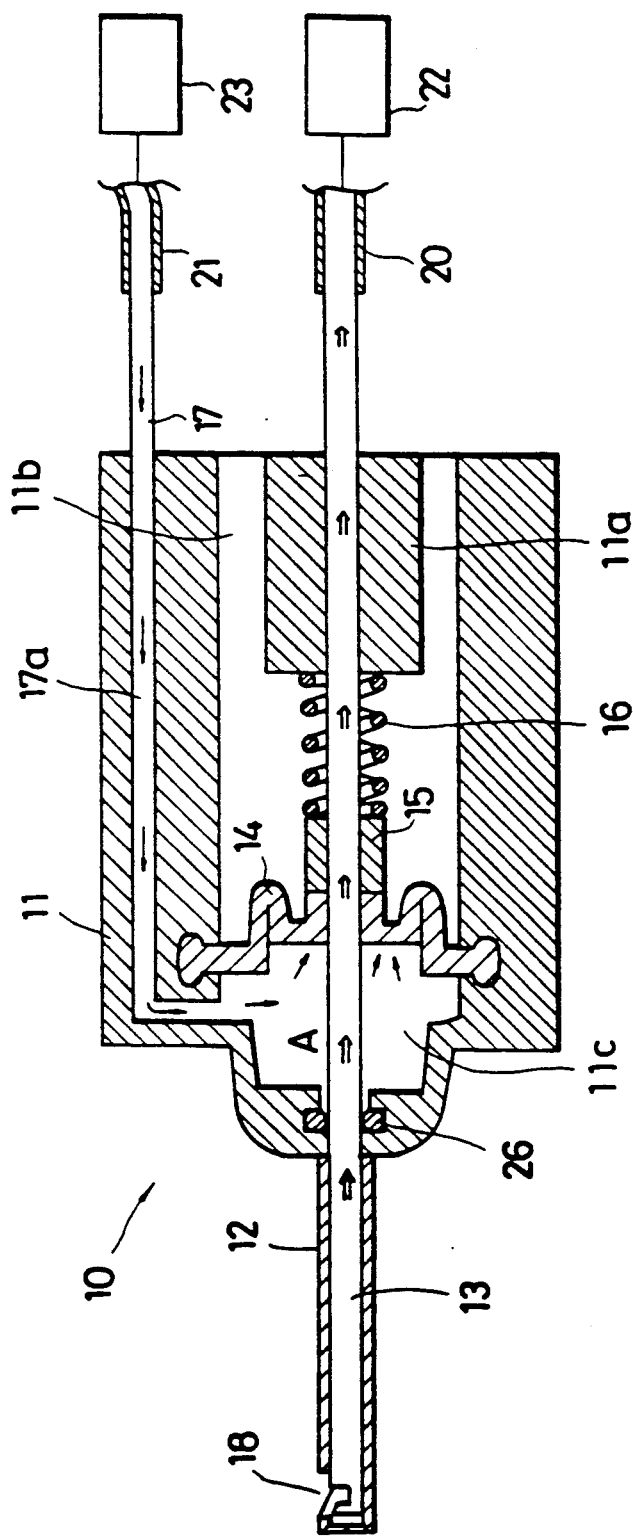
FIG. 1 is a schematic longitudinal sectional view of an ophthalmic surgical cutting instrument according to a first preferred embodiment of present invention.

Referring to FIG. 1, an ophthalmic cutting instrument, according to a first preferred embodiment of the present invention is generally identified by 10 and comprises a casing 11 having a cavity defined therein and having a longitudinal axis, an outer tube 12 having a closed distal end 12a and a proximal end rigidly connected to the casing 11 in alignment with the longitudinal axis of the casing 11, and an inner tube 13 axially movably supported in a manner as will be described later. The casing 11 also provides a grip accessible to the hand of a surgeon. The cavity in the casing 11 is divided into rear and front compartments 11b and 11c by a piston member 15 and an annular diaphragm 14 having a central portion rigidly secured to the piston member 15 and an outer peripheral edge firmly secured to an inner peripheral surface of the casing 11.

The surgical cutting instrument 11 also comprises a biasing spring 16 accommodated within the rear compartment 11b and interposed between the piston member 15 and an insert 11a which is fixed in position so as to close the opening of the rear compartment 11b at the proximal end of the casing 11 and being in alignment with the longitudinal axis of the casing 11, a source of vacuum 22 in communication with the inner tube 13 through a flexible tubing 20, and a source of compressed air 23 which may be, for example, a compressor, and which is in communication with, through a, flexible tubing 21 an air pipe 17 having an air passage 17a defined in the wall of the casing 11, the air passage 17a being in communication with the front compartment 11c.

The piston member 15 is axially movable within the casing 11 between left-hand and right-hand positions, as viewed in FIG. 1, and is normally biased to the left-hand position by the action of the biasing spring 16.

The inner tube 13 has a distal end portion axially slidably accommodated within the outer tube 12 and extends axially from the outer tube 12 to the flexible tubing 20 axially through the diaphragm 14, the piston member 15, the biasing spring 16 and the insert 11a. A substantially intermediate portion of the inner tube 13 extending through the diaphragm 14 and the piston member 15, is rigidly secured to the piston member 15 for movement together therewith. A portion of the inner tube 13 extending through a proximal end wall of the casing 11 is sealed by an O-ring 26 to avoid any possible escape of compressed air introduced into the front compartment 11c in the casing 11.

In the construction so far described, it will readily be understood that, when a single pulse or blast of compressed air from the source of compressed air 23 is introduced into the rear compartment 11c in the casing 11 during the operation of the compressed air source 23, the piston member 15 is driven from the left-hand position or home position, as shown in FIG. 1, towards the right-hand position against the biasing spring 16. When the compressed air source 23 is brought into an inoperative state, the piston member 15 is moved from the right-hand position towards the left-hand, or home position, as biased by the biasing spring 16. In this way, the inner tube 13 undergoes a reciprocating motion relative to the outer tube 12.

Figure 2:
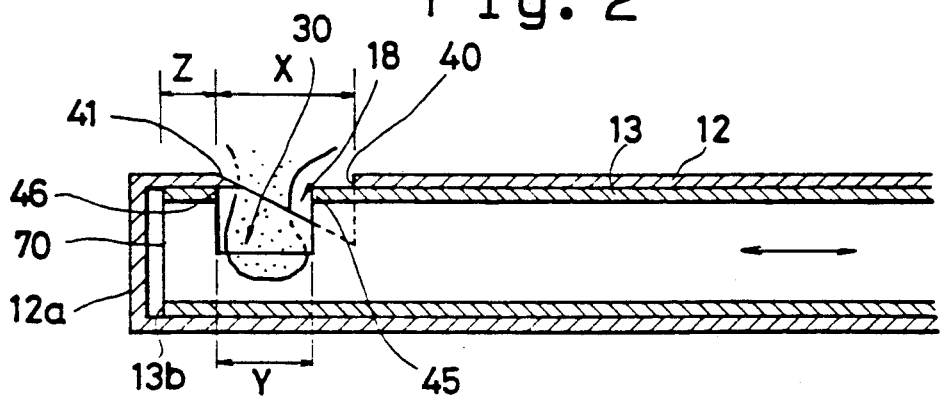
FIG. 2 is a longitudinal sectional view, on an enlarged scale, showing an essential portion of the surgical cutting instrument shown in FIG. 1; with an inner tube held at one position relative to an outer tube.

As best shown in FIGS. 1 and 2, the outer tube 12 having a circular cross-sectional shape has an aperture 18 defined therein, adjacent to the closed distal end 12a thereof, so as to open in a direction generally perpendicular to the longitudinal axis of the outer tube 12 and to be in communication with the hollow of the outer tube 12. Aperture 18 is of a generally triangular shape, as viewed in FIG. 2, and is delimited by a proximal edge 40 and a distal edge 41 opposite to the proximal edge 40.

Similarly, the inner tube 13 has a circular cross-sectional shape, having at its distal end 70 open towards the closed distal end 12a of the outer tube, and also has an aperture 30 defined therein which is adjacent to the distal end 70 so as to open in a direction generally perpendicular to the longitudinal axis of the inner tube 13, and which is in communication with the hollow of the inner tube 13. The aperture 30 in the inner tube 13 is of a generally rectangular shape, as viewed in FIG. 2, and is delimited by a proximal edge 45 and a distal edge 46 which is opposite to the proximal edge 46. The distance Y between the proximal and distal edges 45 and 46 of the aperture 30, along the longitudinal axis of the inner tube 13, is selected to be smaller than the distance X between the proximal and distal edges 40 and 41 of the aperture 18 in the outer tube 12, as measured along the longitudinal axis of the tube system. Distance X is greater than the distance Z between the distal end 70 of the inner tube 13 and the distal edge 46 of the aperture 30 as measured along the longitudinal axis of the tube system.

As best shown in FIG. 2, the proximal edge 40 of the aperture in the outer tube 12 has its edge face lying in a plane perpendicular to the longitudinal axis of the tube system or in the direction in which the inner tube 13 moves, whereas the distal edge 41 of the aperture 18 in the outer tube 12 has an edge face which is downwardly inclined from the outer peripheral surface of the outer tube 12 in a direction towards the longitudinal axis of the tube system and beneath the proximal edge 40 thereof to form an acute angled knife edge. On the other hand, each of the proximal and distal edges 45 and 46 of the aperture 30 in the inner tube 13 has a respective edge face lying in a plane perpendicular to the longitudinal axis of the tube system.

Hereinafter, the manner in which an affected tissue 4, in the eyeball, is cut with the surgical cutting instrument embodying the present invention will be described with reference to FIGS. 2 to 4.

When the vacuum source 22 shown in FIG. 1 is operated, the affected tissue 4 is drawn into the hollow of the inner tube 13 through the aperture 18 in the outer tube 12 and then through the aperture 30 in the inner tube 13 which is aligned with the aperture 18. Thereafter, the compressed air source 23 shown in FIG. 1 is operated to move the piston member 15 from the home position towards the right-hand position with the inner tube 13 consequently moved axially within the outer tube 12 in a direction rightwards as viewed in FIG. 2.

So long as the piston member 15 is held in the home position as shown in FIG. 1, the outer and inner tubes 12 and 13 are positioned such as shown in FIG. 2 with the apertures 18 and 30 aligned with each other. Therefore, the affected tissue 4 protrudes into the hollow of the inner tube 13 through the apertures 18 and 30 as shown by the phantom line in FIG. 2.

Figure 3:
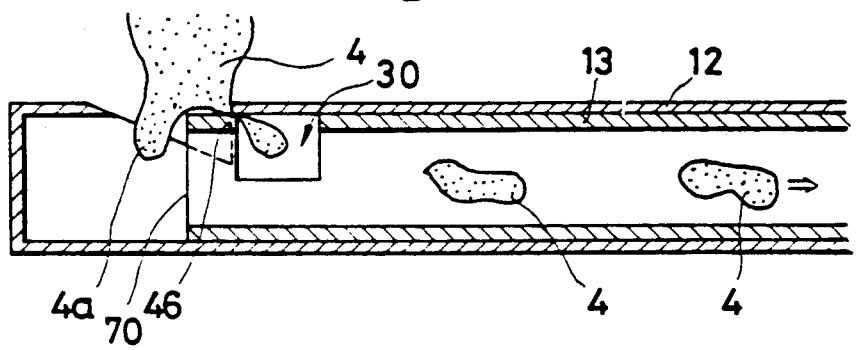
FIGS. 3 and 4 are views similar to FIG. 2 showing the inner tube held at different positions relative to the outer tube, respectively.
Figure 4:
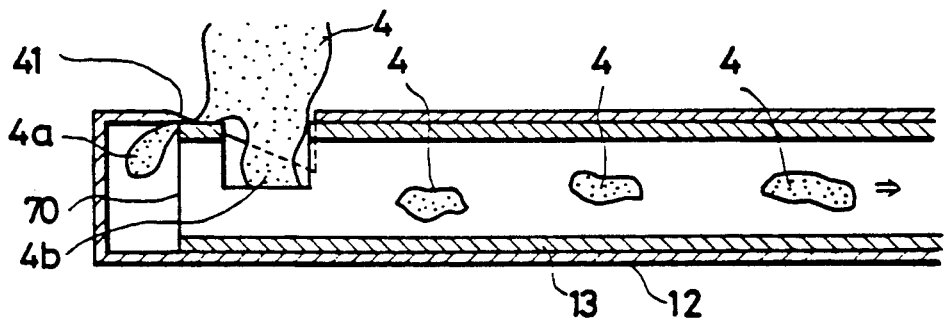

When the piston member 15 is moved from the home position towards the right-hand position as viewed in FIG. 1, the inner tube 13 is axially moved in the rightward direction with the distal edge 46 of the aperture 30 undergoing a substantial scissor action in cooperation with the proximal edge 40 of the aperture 18 in the outer tube 12 to scissor a portion of the affected tissue 4 which protrudes into the hollow of the inner tube 13 through the apertures 18 and 30 as shown in FIG. 3. The portion of the affected tissue 4 which has been scissored or cut, is sucked into the vacuum source 22 through the hollow of the inner tube 13. Since the distal edge 46 and the proximal edge 40 have their respective edge faces lying perpendicular to the longitudinal axis of the tube system, that portion of the affected tissue 4 can be assuredly cut without permitting it to escape from the aligned apertures 18 and 30.

When the distal edge 46 in the inner tube 13 and the proximal edge 40 in the outer tube 12 undergo the scissor action as shown in FIG. 3, a portion of the aperture 18 adjacent to the acute angled distal edge 41 which is opposite to the proximal edge 40, is in communication with the space delimited between the closed distal end 12a of the outer tube 12 and the open distal end 70 of the inner tube 13, thereby allowing another portion 4a of the affected tissue 4 to protrude into such space through the aperture 18 due to the influence of the sucking force developed in the tube system by the vacuum source.

The subsequent deactivation of the compressed air source 23 results in the piston member 16 being displaced from the right-hand position towards the home position by the action of the biasing spring 16 and the inner tube 13 ks consequently moved leftward as viewed in FIGS. 1 to 4. As the inner tube 13 is moved leftward, the distal end 70 of the inner tube 13 undergoes a scissor action in cooperation with the acute angled distal edge 41 in the outer tube to cut another portion 4a of the affected tissue 4. At the moment the portion 4a of the affected tissue 4 is cut from the remainder of the affected tissue 4 by the scissor action of the distal end 70 of the inner tube 13 in cooperation with the acute angled distal edge 41 in the outer tube 12, another portion 4b of the affected tissue 4 protrudes into the hollow of the inner tube 13 through the apertures 18 and 30 as clearly shown in FIG. 4.

By cyclically reciprocating the inner tube 13 relative to the outer tube 12, the affected tissue 4 can be progressively cut. Thus, it will readily be seen that, during the cutting of a portion of an affected tissue 4 incident to the movement of the inner tube 13 in one direction, another portion of the affected tissue 4 can be cut incident to the movement of the inner tube 13 in the opposite direction, and that each reciprocation of the inner tube 13 relative to the outer tube 12 results in sequential cutting of two different portions of the affected tissue 4. It will also be readily understood that the aperture 18 is open, at least partially, at all times during the movement of the inner tube 13 in any one of the opposite directions, thereby avoiding any possible occlusion of the removed tissue which would otherwise occur between the inner and outer tubes 12 and 13.

It is to be noted that, where the direction in which cutting takes place matches with the direction in which suction is effected, one of the opposite edges defining the aperture which is located on the one side conforming to the direction in which the suction takes place may have an edge face lying perpendicular to the longitudinal axis of the tube system, or have a curved edge face. Alternatively, such one of the opposite edges defining the aperture which is located on such one side conforming to the direction in which the suction takes place may have an edge face inclined to permit such edge to represent an acute angled edge other than the right-angled edge.

In addition, the biasing spring 16 which has been described as being interposed between the insert 11a and the piston member 15, may be interposed between the piston member 15 and the front end wall of the casing 11.

Figure 5:
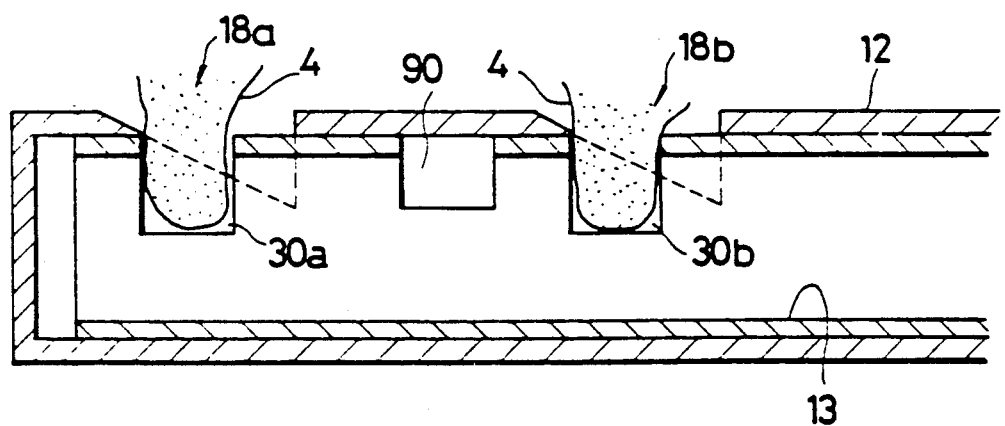
FIG. 5 is a view similar to FIG. 2, showing a modification of the tube system according to the present invention.

Although each of the inner and outer tubes 13 and 12 has been described and shown as having the single aperture 30 and 18, it may have a plurality of apertures. By way of example, as shown in FIG. 5, the outer tube 12 is shown to have two apertures 18a and 18b, and the inner tube 13 is shown to have an equal number of apertures 30a and 30b spaced from each other at a distance determined in consideration with the distance between the apertures 18a and 18b in the outer tube 12. In this modification shown in FIG. 5, the employment of the two apertures 30a and 30b in the inner tube 13 may necessitate an escapement opening 90 defined in the inner tube 13 at a location between the apertures 30a and 30b, and spaced from the distal edge of the aperture 30b at a distance corresponding to the distance Z discussed with reference to FIG. 2, so that the escapement opening 90 can function in a manner substantially similar to the space delimited between the closed distal end of the outer tube 12 and the distal end of the inner tube 13 which has been discussed with particular reference to FIGS. 3 and 4.

According to the foregoing embodiment shown in and described with reference to FIGS. 1 to 5, since the affected tissue in the eyeball can be cut in a direction conforming to the direction in which the suction takes place, the affected tissue can be efficiently removed.

Also, since one of the opposite edges defining the aperture in the outer tube which is located on one side conforming to the direction in which the suction takes place has an edge face lying perpendicular to the longitudinal axis of the tube system, a sharp scissor action can be obtained in cooperation with the inner tube moving inside the outer tube, thereby exhibiting an enhanced cutting performance while eliminating the possibility of a portion of the affected tissue unnecessarily being sandwiched between the inner and outer tubes.

Moreover, since both of the outer and inner tubes have at least one aperture defined therein, and the respective apertures in the outer and inner tubes cooperate with each other to allow the hollow in the inner tube to be in communication with the outside of the tube system, at all times regardless of the position of the inner tube relative to the outer tube, there is substantially no possibility that the affected tissue to be cut may be unnecessarily pulled, thereby avoiding an occurrence of possible malpractice during the surgical operation.

The surgical cutting instrument according to another preferred embodiment of the present invention will now be described.

Figure 6:
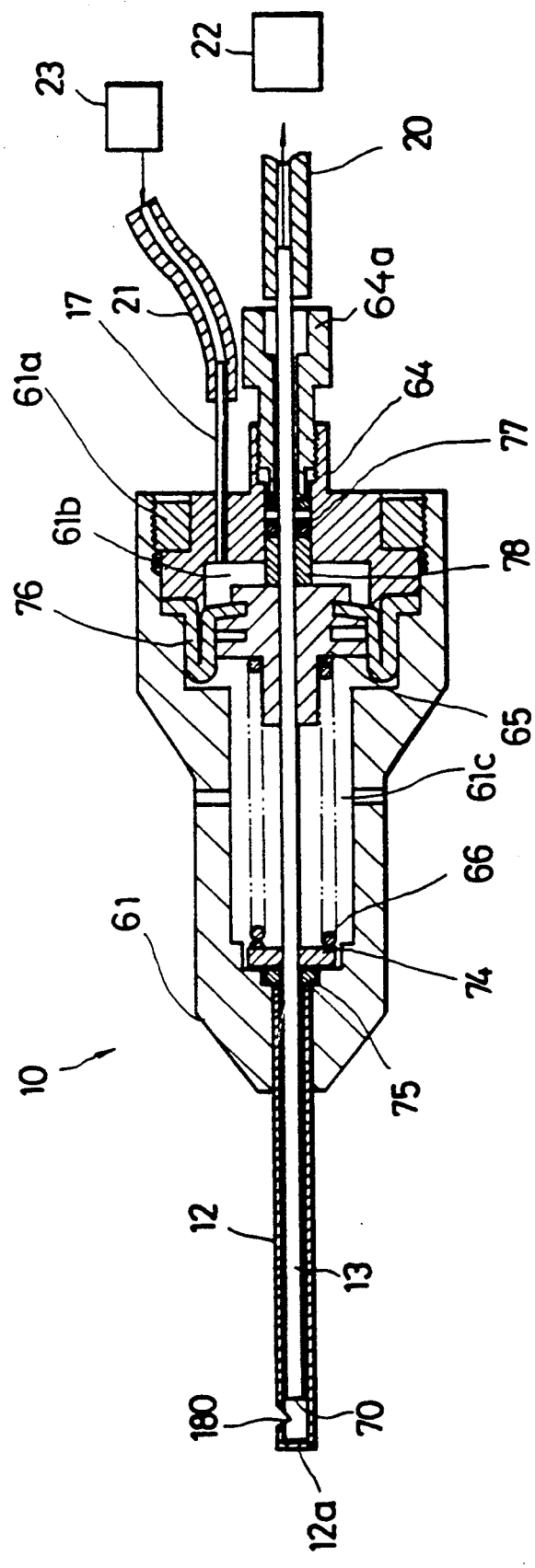
FIG. 6 is a schematic longitudinal sectional view of the ophthalmic surgical cutting instrument according to a second preferred embodiment of the present invention.

Referring first to FIG. 6, there is shown a general construction of the surgical instrument according to the second preferred embodiment of the present invention. The ophthalmic surgical instrument 10 comprises a generally tubular casing 61 which also serves as a grip accessible to the hand of a surgeon, an outer tube 12 extending axially outwardly from one end of the casing 61, and an inner tube 13 axially slidably accommodated within the outer tube 12. The casing 61 has distal and proximal ends opposite to each other and also has an axial cavity defined therein and is open at the distal and proximal ends. The opening at the proximal end of the casing 61 is closed by a rear end lid 64 which is inserted a distance into the cavity and firmly retained in position by means of an annular adjustment ring 61a threaded thereinto. The cavity in the casing 61 is divided into rear and front compartments 61b and 61c by a piston member 65 and an annular diaphragm 76 having an inner peripheral edge rigidly secured to the piston member 15 and an outer peripheral edge firmly clamped between the rear end lid 64 and a shoulder which extends radially inwardly from an inner peripheral surface of the casing 61.

The rear compartment 61b, within the cavity in the casing 61, is delimited between the diaphragm 76, the piston member 65 and the rear end lid 64 and is in communication with the compressed air source 23 through an air pipe 67 and flexible air tubing 21.

The piston member 65 is movable axially within the casing 61 between retracted or home and projected positions, and is normally biased to the retracted or home position by the action of a biasing spring 66. The biasing spring 66 is operatively accommodated within the front compartment 61c and is interposed between the piston member 65 and an annular shoulder extending radially inwardly from the inner peripheral surface of the casing 61. One end of the biasing spring 66 adjacent the distal end of the casing 61 is brought into contact with that annular shoulder through an annular O-ring retainer 74 serving to retain an O-ring 75 in position as will be described later.

In the construction so far described, it will readily be understood that, when a single pulse or blast of compressed air is introduced into the rear compartment 61b in the casing 61, the piston member 65 is driven from the home position, as shown in FIG. 6, towards the projected position against the biasing spring 66, and that when the supply of the pulse or blast of compressed air into the front compartment 66b is interrupted, the piston member 65 is moved back to the home position from the projected position by the action of the biasing spring 66.

The outer tube 62 has a closed distal end 12a and an open proximal end opposite to the closed distal end 12a and is secured to the casing 61 with the proximal end tightly and fixedly inserted into the distal end of the casing 61 in alignment with the cavity in the casing 61. This outer tube 62 has a perforation 180 defined therein at a location adjacent the closed distal end 12a thereof which is in communication with the hollow of the outer tube 12.

The inner tube 13 having open distal and proximal ends is in part accommodated within the outer tube 12, and in part within the cavity in the casing 61, extending completely through the piston member 65 and then through the rear end lid 64. The distal end 70 is situated within the outer tube 12 and the proximal end is situated outside the casing 61. An annular gap between the proximal end of the outer tube 12 and a substantially intermediate portion of the inner tube 13 adjacent the O-ring retainer 74 is completely sealed off by the O-ring 75 which is held in position between it and the O-ring retainer 74 and, accordingly, no air within the front compartment 61c in the casing 61 can enter the outer tube 12.

Figure 7:
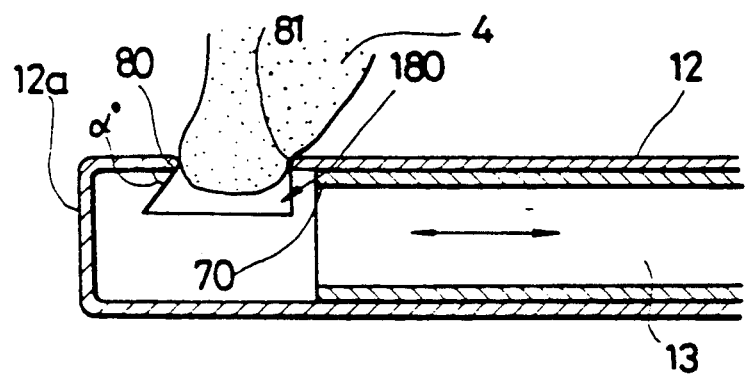
FIG. 7 is a longitudinal sectional view, on an enlarged scale, showing an essential portion of the surgical cutting instrument shown in FIG. 6.

The proximal end of the inner tube 13 extending outwardly from the rear end lid 64 is in turn communicated with the vacuum source 22 through the suction tubing 20. It is to be noted that a portion of the inner tube 13 extending completely through the piston member 65 is fixed thereto while another portion of the inner tube 13 extending completely through the rear end lid 64 is slidable relative thereto. It is also to be noted that the inner tube 13 and the piston member 65 are fixed relative to each other so that, when the piston member 65 is held in the home position, as shown in FIG. 6 as biased by the biasing spring 66, the open distal end of the inner tube 13 may assume a position spaced a distance axially inwardly from the closed distal end of the oute tube 12, and also a slight distance axially inwardly from the aperture 180 defined in the outer tube 12 as best shown in FIG. 7.

However, the home position of the inner tube 13, at which the open distal end 70 thereof is positioned spaced a slight distance axially inwardly from the aperture 180 in the outer tube 12, or the stroke of movement of the piston member 65 and hence that of the inner tube 13, can be adjusted. This is possible because an adjustment screw through which the inner tube 13 loosely extends is threaded into the rear end lid 64 in coaxial relationship with the cavity in the casing 61, with an inner end thereof brought into engagement with the piston member 65 through an O-ring 77 and then through a stopper insert 78. The O-ring 77 serves to any possible escape of air from the rear compartment 61b to the outside through an annular gap present between the inner tube 13 and the rear end lid 64. Thus, it will readily be seen that, when the adjustment screw 64a is turned about the longitudinal axis of the casing 61, the piston member 65 can be moved axially within the cavity in the casing 61 to define the home position for the inner tube 13.

From the foregoing, it is clear that, when a single pulse or blast of compressed air is introduced into the rear compartment 61b from the compressed air source 23, the piston member 65 can be axially driven from the home position towards the projected position against the biasing spring 66 until the piston member 65 is brought into contact with an annular abutment shoulder extending radially inwardly from the casing as shown by 61d, with the inner tube 13 consequently moved axially. At this time, a distal end portion of the inner tube 13 encompassed by the outer tube 12 is moved axially from the home position towards the closed distal end of the outer tube 12. When the supply of the pulse of compressed air into the rear compartment 11b is interrupted, the piston member 65 can be moved back towards the home position by the action of the biasing spring 66, with that distal end portion of the inner tube 13 returning to the home position.

An annular peripheral edge of the open distal end 70 of the inner tube 13 cooperates with the aperture 180 to provide a scissor action to cut an affected tissue in the vitreous in a manner as will be described later. The affected tissue so cut is sucked into the inner tube 13 then communicated with the source of vacuum 22 and is subsequently removed out of the cutting instrument 10.

Figure 8:
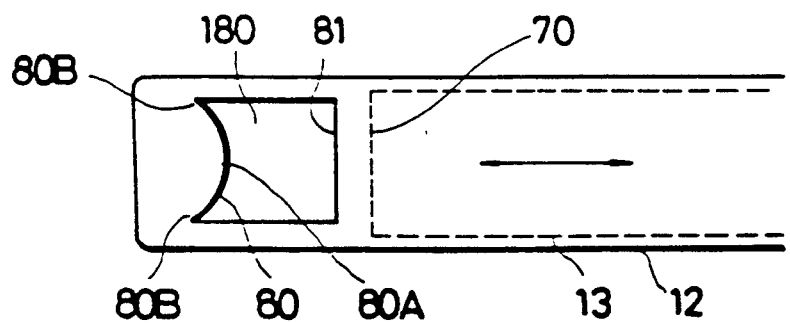
FIG. 8 is a top plan view of the tube system shown in FIG. 7.

With particular reference to FIGS. 7 and 8, the details of the aperture 180 in the outer tube 12 will be described. The aperture 180 is delimited by a distal edge 80 and a proximal edge 81 opposite to the distal edge 80 in a direction parallel to the longitudinal axis of the tube system. The distal edge 80 has an acute angle $a$ relative to the longitudinal axis of the tube system which may be, for example 60°.

As viewed in FIG. 8, the distal edge 80 of the aperture 180 has opposite ends 80B a substantially intermediate portion 80A thereof representing a generally arcuate shape while protruding parallel to the longitudinal axis of the tube system towards the casing 61. On the other hand, the proximal edge 81 of the aperture 180 extends straight in a direction perpendicular to the longitudinal axis of the tube system. Since the substantially intermediate portion 80A of the distal edge 80 is substantially rounded to represent the generally arcuate shape as hereinabove described, the distal edge 80 will not be caught by a portion of the eyeball when the tube system is to be inserted into and withdrawn from the eyeball. This distal end 80 of the unique configuration cooperates with the annular peripheral edge of the open distal end 70 of the inner tube 13 to cut an effected tissue 4 in the eyeball.

The operation of the ophthalmic surgical instrument 10 of the construction shown in and described with reference to FIGS. 6 to 8 will now be described.

When the vacuum source 22 is operated, the affected tissue 4 is drawn into the hollow of the outer tube 12 through the aperture 180 in the outer tube 12. Thereafter, the compressed air source 23 is operated to move the piston member 65 from the home position towards the retracted position with the inner tube 13 consequently moved axially within the outer tube 12 in a direction leftwards as viewed in FIG. 7. As the annular peripheral edge of the distal end 70 of the inner tube 13 traverses the aperture 180 in the outer tube 12, the affected tissue 4 protruding inwardly into the outer tube 12 is cut by the annular peripheral edge of the distal end 70.

Specifically, during the cutting of the affected tissue 4, the annular peripheral edge of the distal end 70 of the inner tube 13 passes beneath a portion 80A of the rounded distal edge 80 intermediate the width thereof, and subsequently beneath the opposite ends 80B of the distal edge 80, thereby accomplishing a progressive scissor action which cuts the affected tissue 4 smoothly. Even though a satisfactory scissor action cannot be obtained at the intermediate portion 80A of the distal edge 30 during the passage of the annular peripheral edge of the distal end 70 of the inner tube 13, a portion of the affected tissue 4, which was could not be cut satisfactorily at the intermediate portion 80A of the distal edge 80, can be pushed towards the opposite ends 80B of the distal edge 80 so that the affected tissue 4 can be cut assuredly at a stroke. The removed tissue 4 can be sucked towards the vaccum source 22 through the inner tube 13 and then through the suction tubing 20.

The rounded distal edge 80 of the aperture 180 in the outer tube 12 can advantageously provide an increased safety factor which may be appreciated during the insertion and subsequent withdrawal of the surgical cutting instrument 10 into and from the eyeball.

Figure 9:
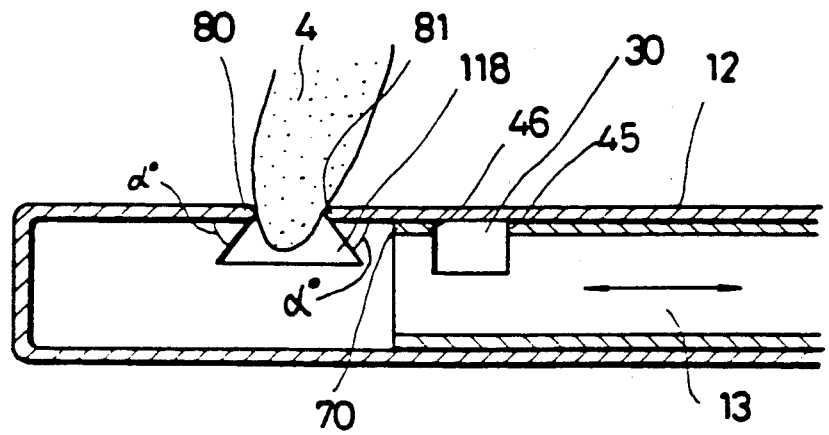
FIGS. 9 to 14 are views similar to FIG. 7 showing different modifications of the tube system shown in FIG. 7, respectively.
Figure 10:
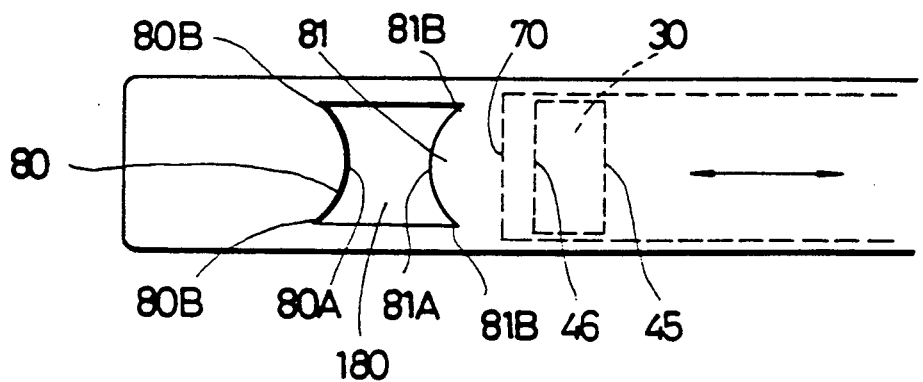

FIGS. 9 and 10 illustrate a modification of the tube system, which can be employed in the above described surgical cutting instrument according to any one of the first and second preferred embodiments of the present invention. According to this modification, the proximal edge 81 of the aperture 180 opposite to the distal edge 80 of generally arcuate configuration, as hereinbefore described, is so shaped as to resemble the shape of the distal edge 80 in an opposite sense. Specifically, both the distal edge 80 and the proximal edge 81 have an equal angle α which may be, for example, 60° relative to the longitudinal axis of the tube system. As is the case with the distal edge 80, the proximal edge 81 has opposite ends 81B, a substantially intermediate portion 81A thereof protruding towards the opposite distal edge 80 while representing a generally arcuate shape as viewed in FIG. 10.

On the other hand, the inner tube 13 is substantially identical in construction with that shown in FIGS. 2 and has the generally rectangular aperture 30 defined therein adjacent the open distal end 70. So fas as illustrated, the open distal end 70 and the distal and proximal edges 46 and 45 defining the rectangular aperture 30 in the inner tube 13 lie in respective planes perpendicular to the longitudinal axis of the tube system.

The surgical cutting instrument 10 employing the inner and outer tubes 12 and 13 which are modified as shown in and described with reference to FIGS. 9 and 10 is operated in a manner substantially similar to that shown in and described with reference to FIGS. 1 to 3. More specifically, during the movement of the inner tube 13 in the leftward direction as viewed in FIGS. 9 and 10, the annular peripheral edge of the distal end 70 of the inner tube 13 passes beneath a portion 80A of the rounded distal edge 80 intermediate the width thereof and subsequently beneath the opposite ends 80B of the distal edge 80, thereby accomplishing a progressive scissor action for cutting a portion of the affected tissue 4 smoothly. Even though a satisfactory scissor action cannot be obtained at the intermediate portion 80A of the distal edge 30, during the passage of the annular peripheral edge of the distal end 70 of the inner tube 13 that portion of the affected tissue 4 which could not be cut satisfactorily at the intermediate portion 80A of the distal edge 80, can be pushed towards the opposite ends 80B of the distal edge 80 so that the affected tissue 4 can be cut assuredly at a stroke.

As a portion of the affected tissue 4 is cut by the annular peripheral edge of the distal end 70 of the inner tube 13 in cooperation with the distal edge 80 of the aperture 180, another portion of the affected tissue 4 protrudes into the rectangular aperture 30 through the aperture 180 which is then partially aligned with the rectangular aperture 30 and, therefore, the other portion of the affected tissue 4 can also be cut by the proximal edge of the aperture 30 in cooperation with the distal edge 80 of the aperture 180. Even though a satisfactory scissor action cannot be obtained at the intermediate portion 80A of the distal edge 80, during the passage of the proximal edge 45 of the aperture 30 in the inner tube 13, that portion of the affected tissue 4 which could not be cut satisfactorily at the intermediate portion 80A of the distal edge 80, can be pushed towards the opposite ends 80B of the distal edge 80 so that the affected tissue 4 can be cut assuredly at a stroke.

During the movement of the inner tube 13 in the opposite, rightward direction, a further portion of the affected tissue 4 is cut in a similar fashion. In other words, the distal edge 46 of the aperture 30 in the inner tube 13 passes beneath the portion 81A of the rounded proximal edge 81 intermediate the width thereof, and subsequently beneath the opposite ends 81B of the proximal edge 81, thereby accomplishing a progressive scissor action for cutting the further portion of the affected tissue 4 smoothly. Even though a satisfactory scissor action cannot be obtained at the intermediate portion 81A of the proximal edge 81 during the passage of the distal edge 46 of the aperture 30 in the inner tube 13, that portion of the affected tissue 4 which could not be cut satisfactorily at the intermediate portion 81A of the proximal edge 81, can be pushed towards the opposite ends 81B of the proximal edge 81 so that the affected tissue 4 can be cut assuredly at a stroke.

As a portion of the affected tissue 4 is cut by the distal edge 46 of the aperture 30 in the inner tube 13 in cooperation with the proximal edge 81 of the aperture 180, a still further portion of the affected tissue 4 protrudes through the aperture 180 into a space delimited between the closed distal end 12a of the outer tube 12 and the open distal end of the inner tube 13 in readiness for the cutting thereof during the next succeeding cycle.

By cyclically reciprocating the inner tube 13 relative to the outer tube 12, the affected tissue 4 can be progressively cut.

In either case, the removed tissue 4 can be sucked towards the vaccum source 22 through the inner tube 13 and then through the suction tubing 20.

Figure 11:
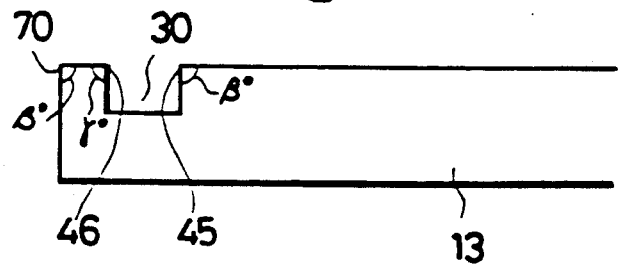

It is to be noted that each of the proximal and distal edges 45 and 46 of the aperture 70, and the distal end 70 of the inner tube 13 has a respective angle β° and α°, as shown in FIG. 11, which may be chosen in consideration of the angle α° of the distal edge 80 of the aperture 180 so as to be of a particular value which is effective a smooth and efficient.

Figure 12:
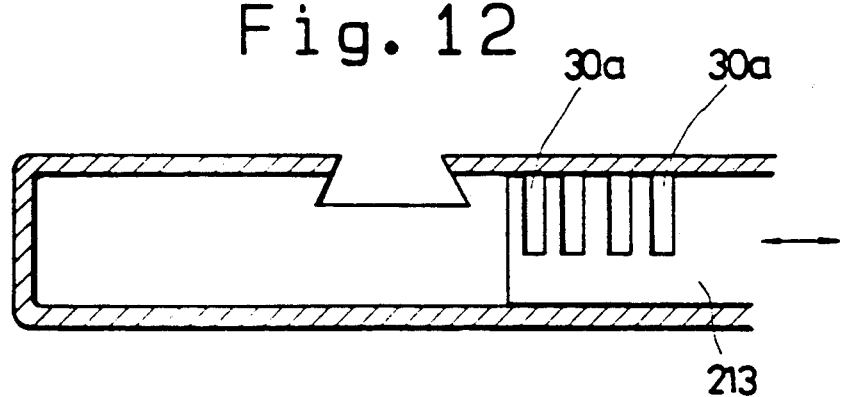

In another modification shown in FIG. 12, instead of the use of the single rectangular aperture 30, a plurality of equally spaced rectangular apertures 30a are defined in the peripheral wall of the inner tube 13 adjacent the distal end thereof to enhance the cutting performance.

Figure 13:
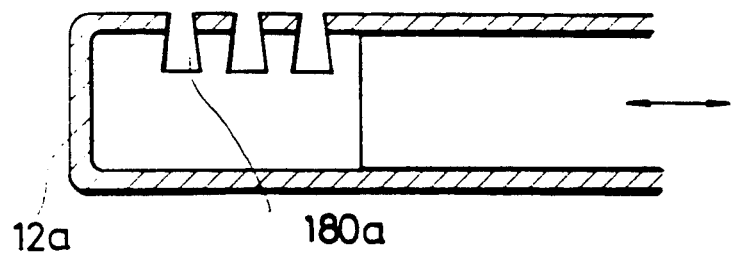

In a further modification shown in FIG. 13, instead of the use of the single aperture 180 in the outer tube 12, a plurality of equally spaced apertures 180a, each similar in shape to the aperture 180, are defined in the peripheral well of the outer tube 12 adjacent the distal end thereof.

Figure 14:
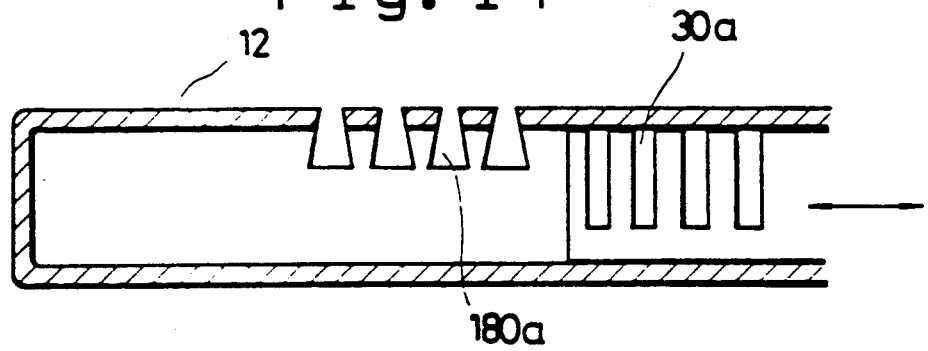

In a still further modification shown in FIG. 14, not only does the outer tube 12 have a plurality of equally spaced apertures 180a, each similar in shape to the aperture 180, defined in the peripheral wall thereof, but also the inner tube 13 has a plurality of equally spaced rectangular apertures 30a which are defined in the peripheral wall thereof to further enhance the cutting performance.

According to the second preferred embodiment of the present invention, not only can the surgical cutting instrument exhibit effects similar to those afforded by the surgical cutting instrument according to the first preferred embodiment of the present invention, but an additional effect that the provision of the rounded distal and/or proximal edges defining the aperture in the outer tube can provide is a substantially increased safety factor, thereby avoiding any possible retraumatization to the eyeball.

Although the present invention has been fully described in connection with the preferred embodiments thereof and with reference to the accompanying drawings which are used only for the purpose of illustration, those skilled in the art will readily conceive numerous changes and modifications within the framework of obviousness upon the reading of the specification herein presented of the present invention. For example, any one of the modifications shown and described in connection with the second preferred embodiment of the present invention can be employed in the surgical cutting instrument according to the first preferred embodiment of the present invention.

Also, the surgical cutting instrument according to the present invention can be equally utilized in any surgical operation other than the ophthalmic operation.

Accordingly, such changes and modifications are, unless they depart from the spirit and scope of the present invention as delivered from the claims annexed hereto, to be construed as included therein.

What is claimed is:

1. A surgical cutting instrument which comprises:
    an outer tubular member having a closed distal end, a first aperture defined therein adjacent to the closed distal end and being in communication with the hollow of the outer tubular member, and a longitudinal axis, said aperture being delimited by opposed distal and proximal edges;
    an inner tubular member, slidably disposed in the outer tubular member, having a longitudinal axis parallel to the longitudinal axis of the outer tubular member and an open distal end, wherein the inner tubular member slides along its longitudinal axis between first and second positions and cooperates with the outer tubular member to provide a scissor action thereby cutting a portion of an object which has protruded inwardly through the aperture in the outer tubular member during a reciprocating motion of the inner tubular member relative to the outer tubular member;
    suction means for protruding inwardly said object through the aperture in the outer tubular member and sucking said portion through the hollow of the inner tubular member to the outside of the instrument; and wherein
    said inner tubular member has first and second opposed edges defined therein, adjacent to the open distal end, each of said first and second edges having an edge face lying generally perpendicular to the longitudinal axis of the inner tubular member, said first edge being utilized to cut a first portion of the object which has protruded inwardly through the aperture due to the suction means during the axial movement of the inner tubular member from the first position towards the second position and the second edge being utilized to cut a second portion of the object which has protruded inwardly through the aperture due to the suction means during the axial movement of the inner tubular member from the second position towards the first position.

2. The instrument as claimed in claim 1, wherein each of the distal and proximal edges delimiting the aperture in the outer tubular member has an edge face inclined downwardly towards the longitudinal axis of the outer tubular member such that each of the edge faces and a plane including the longitudinal axis of the outer tubular member form an acute angle.

3. The instrument as claimed in claim 2, wherein said inner tubular member has a first aperture defined therein adjacent to the open distal end thereof, said first aperture in the inner tubular member being delimited by distal and proximal edges which are opposite to each other in a direction parallel to the longitudinal axis of said inner tubular member, and wherein said first and second edges in the inner tubular member are the distal and proximal edges delimiting the first aperture in the inner tubular member, respectively.

4. The instrument as claimed in claim 1, wherein at least the distal edge of the first aperture in the outer tubular member is rounded with a substantially intermediate portion thereof protruding towards the proximal edge of the first aperture in the outer tubular member.

5. The instrument as claimed in claim 1, wherein the distal and proximal ends of the first aperture in the outer tubular member are rounded with respective substantially intermediate portions protruding towards each other in a direction parallel to the longitudinal axis of the outer tubular member.

* * * * *